United States Patent [19]

Mastaler

[11] Plant 4,187

[45] Jan. 17, 1978

[54] SCHEFFLERA

[75] Inventor: John Mastaler, Hialeah, Fla.

[73] Assignee: Schefflera, Unlimited Inc., Coconut Grove, Fla.

[21] Appl. No.: 696,543

[22] Filed: June 16, 1976

[51] Int. Cl.[2] ..... A01H 5/12

[52] U.S. Cl. ..... Plt./88

[58] Field of Search ..... Plt./88

[56] References Cited

PUBLICATIONS

Exotica 3, Graf, 1963, Roehrs Co., Rutherford, N.J., p. 250.

*Primary Examiner*—Robert E. Bagwill

*Attorney, Agent, or Firm*—Frank B. Robb

[57] ABSTRACT

There is disclosed a new and distinct variety of *Brassaia actinophylla,* more commonly known as Schefflera, characterized by the extensive and attractive variegations which were found in the parent and which are dominant in reproductions.

3 Drawing Figures

FIELD OF THE INVENTION

This invention relates to Schefflera plants and, more particularly, to a variegated Schefflera.

BACKGROUND OF THE INVENTION

Schefflera has been a popular plant because of its vigorous, rapid growth with solid green foliage and hardy habit, providing a decorative as well as tree-like appearance.

The instant variety which I discovered among plants growing on my property in Hialeah, Fla., was closely observed from the time I first found the same and since the variegation made it stand out from other Schefflera growing nearby.

Particular study was made of the leaves and arrangement of those leaves on the trunk which disclose that a particular leaf area was mottled with variegation and I therefore cut this particular plant back with the purpose of preserving the variegated leaves and those with the most variegation particularly.

Further observation disclosed that the branches of the plant were very close together and thus provide a greater number of leaves.

Successive asexual reproduction performed by me enabled me to select outstanding examples of variegation and also those plants with close noded arrangement of branches. This characteristic serves to make the display of color more pronounced and presents an almost marble-like appearance with wide color range from green to yellows of various shades.

In some instances there is an almost rosy coloration in the overall appearance of a plant which is in full leaf, because the stems themselves are quite pink.

The accompanying drawings show a typical specimen of my new variety of Schefflera Plant disclosing the dense arrangement of the foliage, a close up disclosing the wide differences in variegation of particular leaves; and the close noded positions of the leaves and branches at their connections to the trunk likewise.

One of the outstanding characteristics of my new variety of Schefflera is that the trunk, stems and leaves all display this variegation characteristic and the leaves are in all cases substantially thicker than the leaves of non-variegated Schefflera commonly grown, the leaves of my new variety usually being approximately one third thicker than such known variety.

This characteristic appears to make the leaves more resistant to certain insects such as spider mites and is an important aspect of my new variety.

Continued asexual reproduction of my new variety discloses that plants are much hardier, resisting cold weather well, the foliage remains all along the trunk and when the plant has grown to a height of 4 to 6 feet, a large number of leaf stems are observed and because they are close together they present an almost rosy appearance.

One of the most outstanding advantages of my new variety is that it grows so vigorously and the leaves and branches are so close together that a single stem or trunk may be sold in pot plant instead of the usual two or three which are normally sold of the common Schefflera.

The variegated Schefflera is closer noded than regular Schefflera, the shape of the plant is very compact in the sense that the nodes are closer together than is typical of the regular Schefflera giving a tighter appearance at all stages of growth to the plant and tends to hold the bottom foliage longer.

The following is a detailed description of my new variety of Schefflera Plant, with color terminology in accordance with Munsell Color Cascade, except where general color terms of ordinary dictionary significance are suitable, based on observations made of a specimen grown in a nursery near Boynton Beach, Fla.

Parentage: A sport of *Brassaia actinophylla.*

Propagation: Holds its distinguishing characteristics through successive propagation by meristematic splitting.

Plant:

*Form.*—Upright — very compact.

*Growth.*—Vigorous.

*Blooming habits.*—Has not bloomed or seeded.

Height:

*Approximate measurements of average.*—6 to 8 feet and higher.

Spread: 4 foot to 6 foot in large plants.

FOLIAGE

Leaflets: 10–14 per rack.
Size: Very large.
Quantity: Abundant.
New foliage color:
*Upper side.*—Variegated — yellow #26-3 and green #1-15.
*Under side.*—Variegated: yellow #22-7 to green #21-14.
Shape: Oblanceolate.
Texture:
*Upper side.*—Leathery; flat.
Ribs and veins: Ordinary.
Edge: Smooth.
Serration: Single; large.
Leaf Stem:
*Color.*—Variegated like leaf with marbled rose color.
Disease resistance: Resistant to spider mites.

WOOD (NEW)

Color: Green #26-3 to yellow #21-15 — rose marbled #40-11. When cut, marbling can be seen throughout.
Bark: Smooth.

WOOD (OLD)

Same as new wood at top, changing to gray at base of trunk.
Bark: Smooth.

I claim:

1. A new and distinct variety of Schefflera Plant of the species *Brassaia actinophylla* substantially as herein shown and described characterized particularly as to novelty by the overall variegation of leaves, stems, and trunk from green to yellow and with stems of rosy marbled appearance, close noded position of stems and compact upright rapid growth, with leaves of leathery, thick form, vigorous growth with leaves continuing to hang on at lower portion of plant.

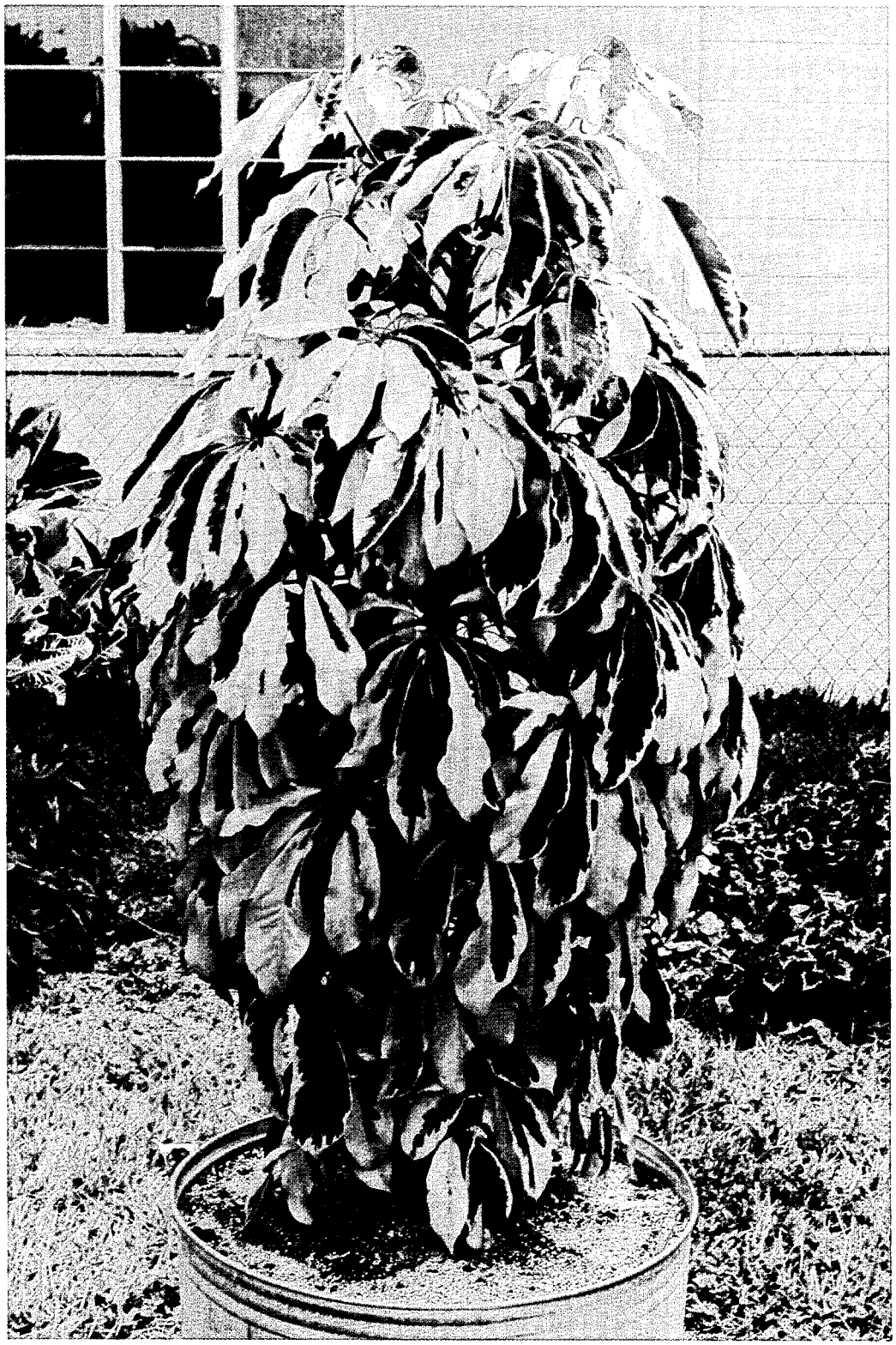

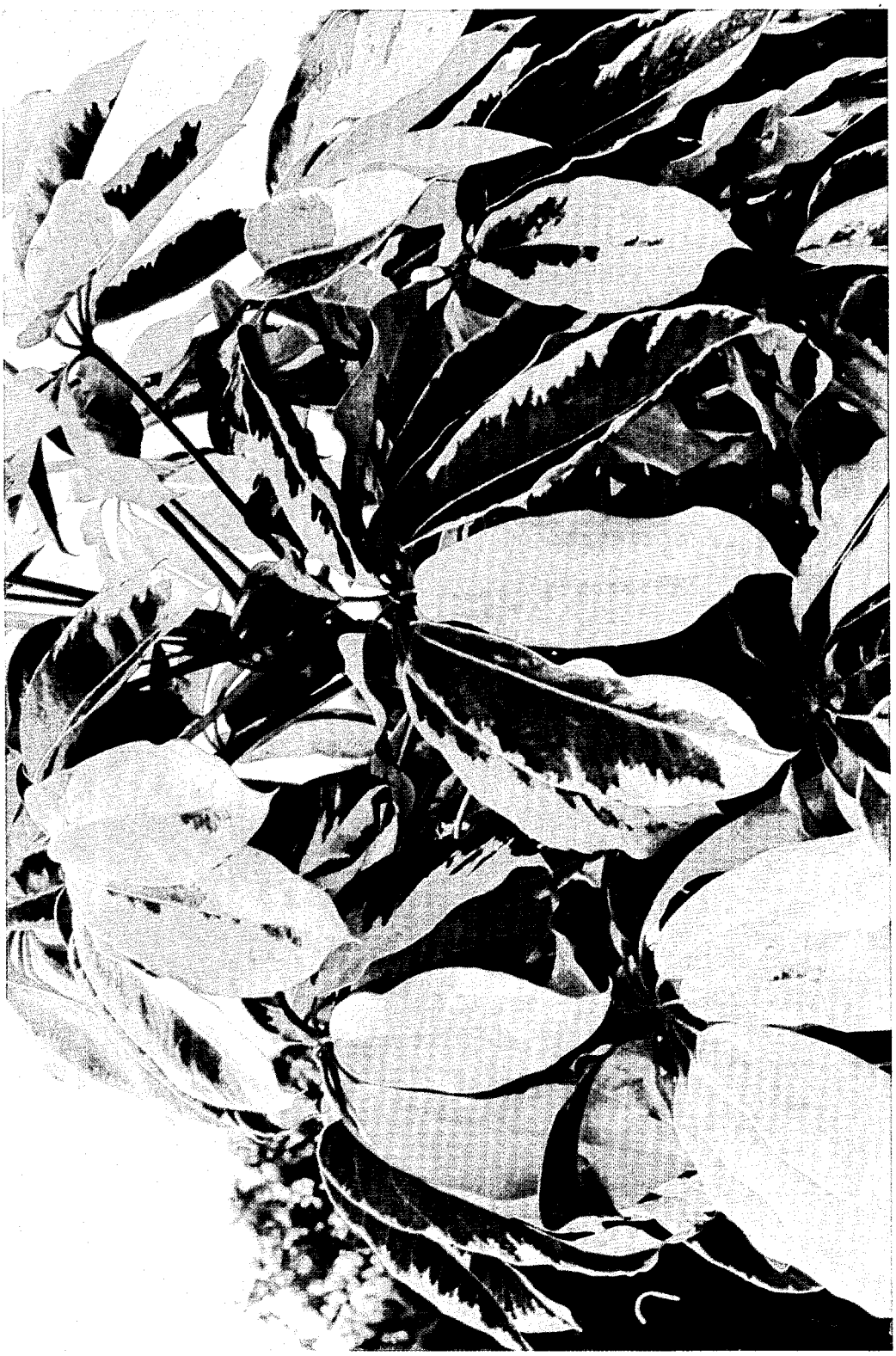

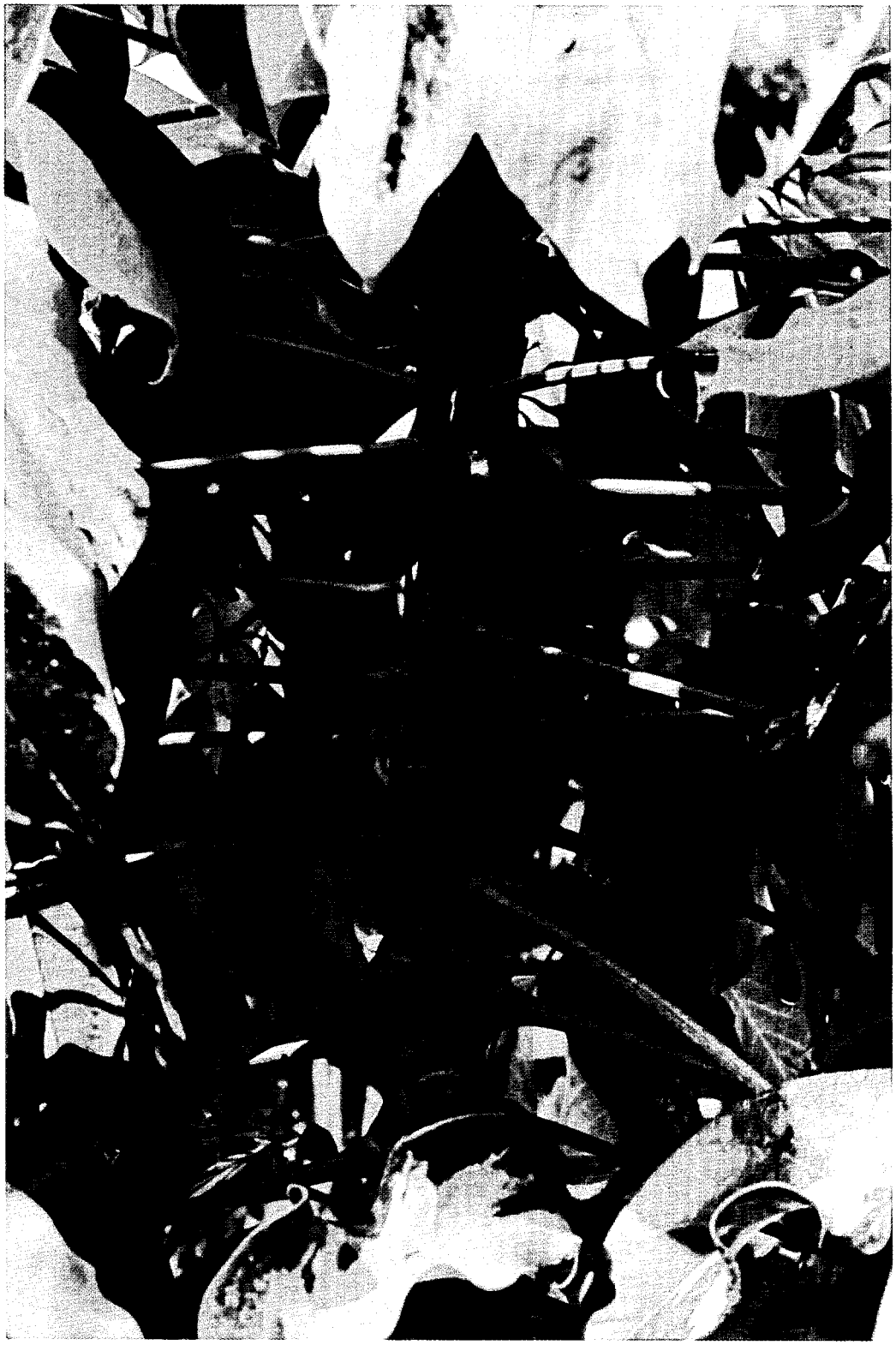

* * * * *